(12) United States Patent
Szabados et al.

(10) Patent No.: US 11,064,888 B2
(45) Date of Patent: Jul. 20, 2021

(54) DETECTION OF BIKING, WALKING, AND RUNNING

(71) Applicant: Intel Corporation, Santa Clara, CA (US)

(72) Inventors: Steven P. Szabados, San Francisco, CA (US); Andrew A. Stirn, San Francisco, CA (US); Timothy Melano, San Francisco, CA (US); Nathan R. Kowahl, San Francisco, CA (US); Christopher Verplaetse, San Francisco, CA (US); Colt Stander, San Francisco, CA (US)

(73) Assignee: Intel Corporation, Santa Clara, CA (US)

(*) Notice: Subject to any disclaimer, the term of this patent is extended or adjusted under 35 U.S.C. 154(b) by 0 days.

(21) Appl. No.: 16/662,312

(22) Filed: Oct. 24, 2019

(65) Prior Publication Data

US 2020/0155901 A1    May 21, 2020

Related U.S. Application Data

(62) Division of application No. 15/022,013, filed as application No. PCT/US2014/063943 on Nov. 4, 2014, now Pat. No. 10,456,622.
(Continued)

(51) Int. Cl.
*A61B 5/11* (2006.01)
*A61B 5/00* (2006.01)
(Continued)

(52) U.S. Cl.
CPC .......... *A61B 5/0024* (2013.01); *A61B 5/1123* (2013.01); *A61B 5/681* (2013.01); *A63B 24/0062* (2013.01); *A63B 71/0619* (2013.01); *G01P 15/00* (2013.01); *A61B 5/0245* (2013.01); *A61B 5/02055* (2013.01); *A61B 5/02438* (2013.01); *A61B 5/4266* (2013.01); *G16H 20/30* (2018.01); *G16H 40/63* (2018.01); *G16H 40/67* (2018.01)

(58) Field of Classification Search
CPC ..... A61B 5/0024; A61B 5/1123; A61B 5/681; A63B 24/0062; A63B 71/0619; G01P 15/00
See application file for complete search history.

(56) References Cited

U.S. PATENT DOCUMENTS

2006/0167387 A1    7/2006  Buchholz et al.
2008/0077620 A1*   3/2008  Gilley ................... A63B 22/02
(Continued)

OTHER PUBLICATIONS

Final Office Action in U.S. Appl. No. 15/022,013 dated Nov. 13, 2018, 11 pages.
(Continued)

*Primary Examiner* — Daniel L Cerioni
(74) *Attorney, Agent, or Firm* — Patent Capital Group

(57) ABSTRACT

A wearable device automatically identifies an activity in which a user of the device is engaged while wearing the device. The wearable device receives motion data of the user collected during the activity and determines a magnitude and a frequency of the motion data. Based on the magnitude and frequency of the motion data, the wearable device identifies the activity in which the user is engaged.

14 Claims, 14 Drawing Sheets

Related U.S. Application Data

(60) Provisional application No. 61/899,848, filed on Nov. 4, 2013.

(51) Int. Cl.

| | | |
|---|---|---|
| *A63B 24/00* | (2006.01) | |
| *A63B 71/06* | (2006.01) | |
| *G01P 15/00* | (2006.01) | |
| G16H 40/63 | (2018.01) | |
| A61B 5/024 | (2006.01) | |
| A61B 5/0205 | (2006.01) | |
| A61B 5/0245 | (2006.01) | |
| G16H 20/30 | (2018.01) | |
| G16H 40/67 | (2018.01) | |

(56) References Cited

U.S. PATENT DOCUMENTS

| | | |
|---|---|---|
| 2011/0054359 A1 | 3/2011 | Sazonov et al. |
| 2012/0232432 A1 | 9/2012 | Kahn et al. |
| 2013/0029681 A1 | 1/2013 | Grokop |
| 2013/0191034 A1 | 7/2013 | Weast et al. |
| 2014/0167973 A1 | 6/2014 | Letchner et al. |
| 2015/0051867 A1* | 2/2015 | Choi .......... G01C 22/006 702/160 |
| 2016/0206921 A1 | 7/2016 | Szabados et al. |

OTHER PUBLICATIONS

International Search Report and Written Opinion in International Application No. PCT/U2014/063943 dated Feb. 13, 2015.
Mouser Electronics Product Finder.
Non Final Office Action in U.S. Appl. No. 15/022,013 dated Jun. 14, 2018, 12 pages.
Notice of Allowance in U.S. Appl. No. 15/022,013 dated Jun. 20, 2019, 7 pages.

* cited by examiner

DETECTION OF BIKING, WALKING, AND RUNNING

CROSS REFERENCE TO RELATED APPLICATIONS

This application is a divisional application of U.S. patent application Ser. No. 15/022,013 filed on Mar. 15, 2016, and entitled "Detection of Biking, Walking, and Running" which application is a national stage application under 35 U.S.C. § 371 of PCT International Application Serial No. PCT/US2014/063943, filed on Nov. 4, 2014 and entitled "Detection of Biking, Walking, and Running", which application claims the benefit of U.S. Provisional Application 61/899,848, filed Nov. 4, 2013, which are incorporated by reference in their entirety in the disclosure of this application.

BACKGROUND

1. Field of Art

The disclosure generally relates to wearable devices, and in particular to identification of particular activities of a user wearing a device.

2. Description of the Related Art

Wearable technology enables people to interact with technology in a convenient manner, since it can be present on the body in the context of all lifestyle activities. Wearable devices can measure the user and the user's surroundings continuously, and provide immediate information and feedback to the user any time the device is worn. However, a wearable device typically provides more useful information to a user when the wearable device accounts for a particular activity in which the user is engaged. To identify the activity in which the user is engaged, a user generally currently must interact with the device to explicitly identify the activity in which the user is engaged. Such user interaction is inconvenient to the user of the device. Furthermore, as the user may forget to input a different activity when changing between activities or may not input different activities when pausing an activity (e.g., while waiting at a stoplight while bicycling or running), relying on user input to determine an activity in which the user is engaged may lead to inaccurate calculations.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

Figure (FIG. 1 illustrates one embodiment of a wearable device with a display.

DETAILED DESCRIPTION

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

One embodiment of a disclosed system and method automatically identifies for a user wearing a wearable device an activity in which the user is engaged. Identified activities including walking, running and bicycling. In some embodiments, the identification is made based on data from a motion sensor. In some embodiments, the identification is made without input from any additional sensors.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Example Device Configuration

Figure 1:
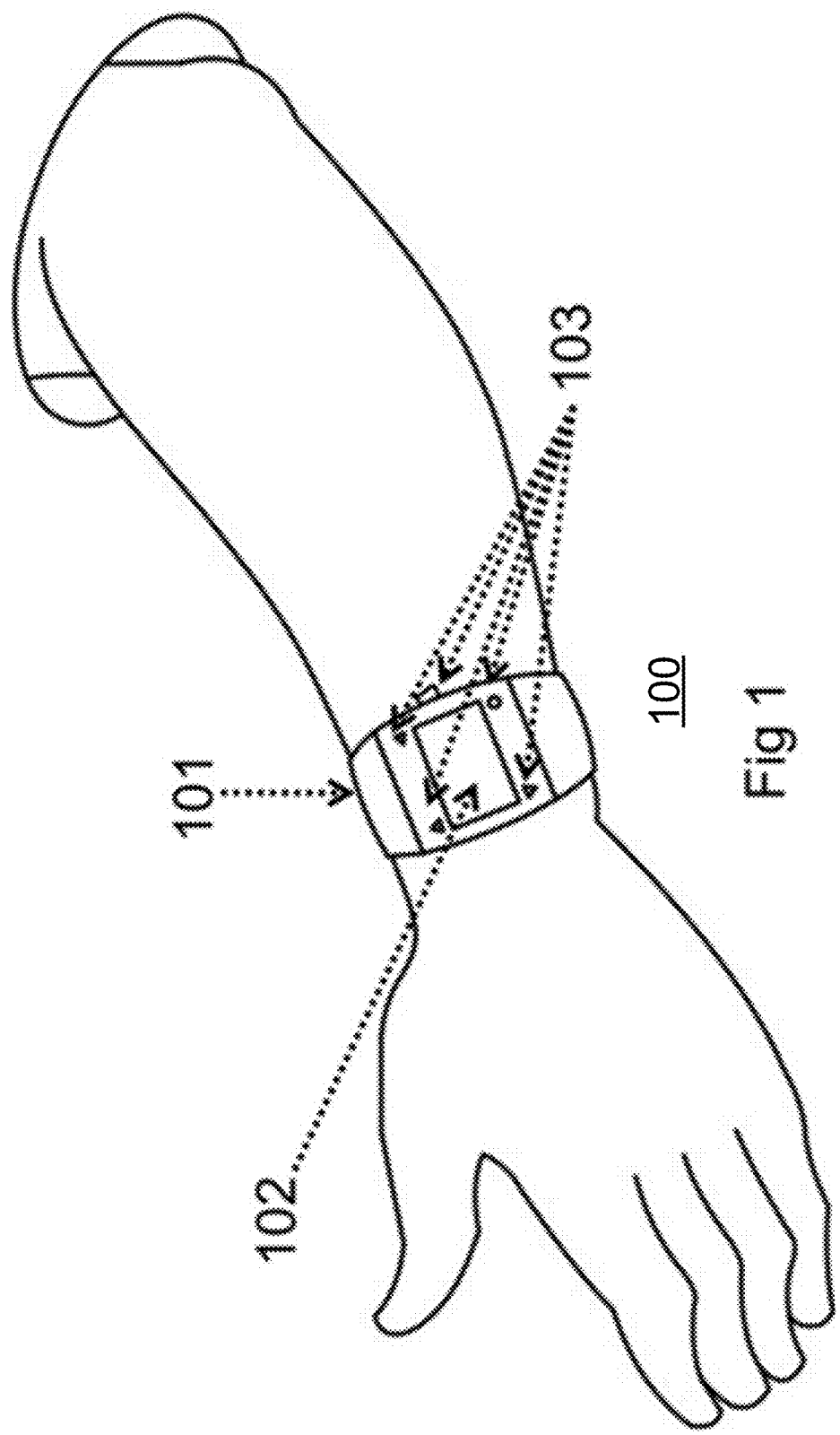

Figure (FIG. 1 illustrates an embodiment of a wearable device 100. The exemplary device 100 is worn on the wrist of a user, although other form factors or designed wear locations of the wearable device 100 may alternatively be used. For example, methods described herein may be implemented in arm-worn devices, head-worn devices, clip-on devices, and so forth. A fastening system 101 is shown, although the device may alternatively be portable instead of worn. For example, the device 100 may be carried in a pocket of a worn garment or affixed to a bag strap or belt. The fastening system 101 may be removable, exchangeable or customizable.

The device 100 includes a display (or screen) 102 and user interaction points 103. The display 102 and user interaction points 103 may be separate components of the device 100, or may be a single component. For example, the display 102 may be a touch-sensitive display configured to receive user touch inputs and display information to the user. The wearable device 100 may also have a display element such as 102 without interaction points 103, or interaction points 103 without a display element 102.

Figure 2:
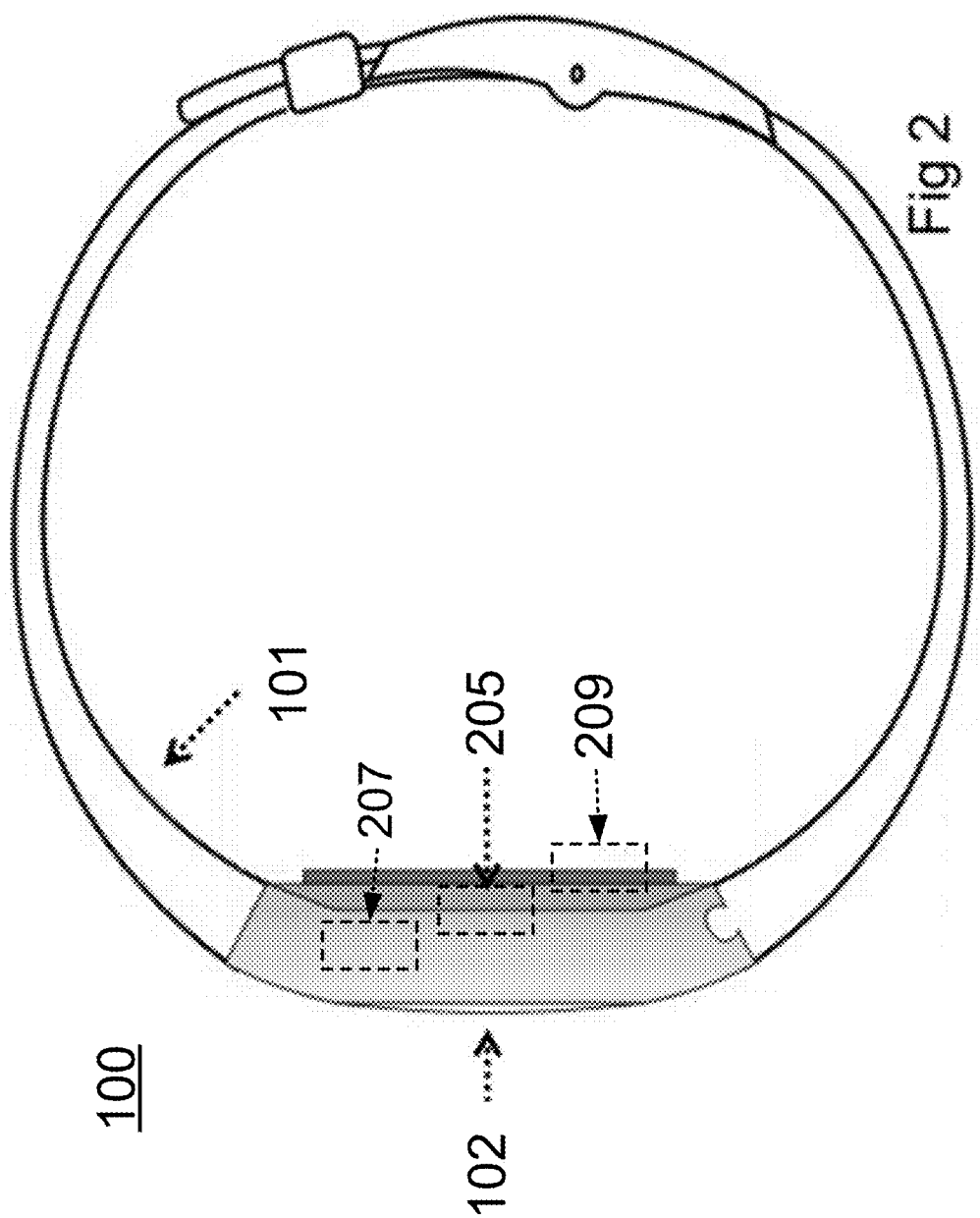
FIG. 2 illustrates another view of an embodiment of a wearable device.
Figure 3:
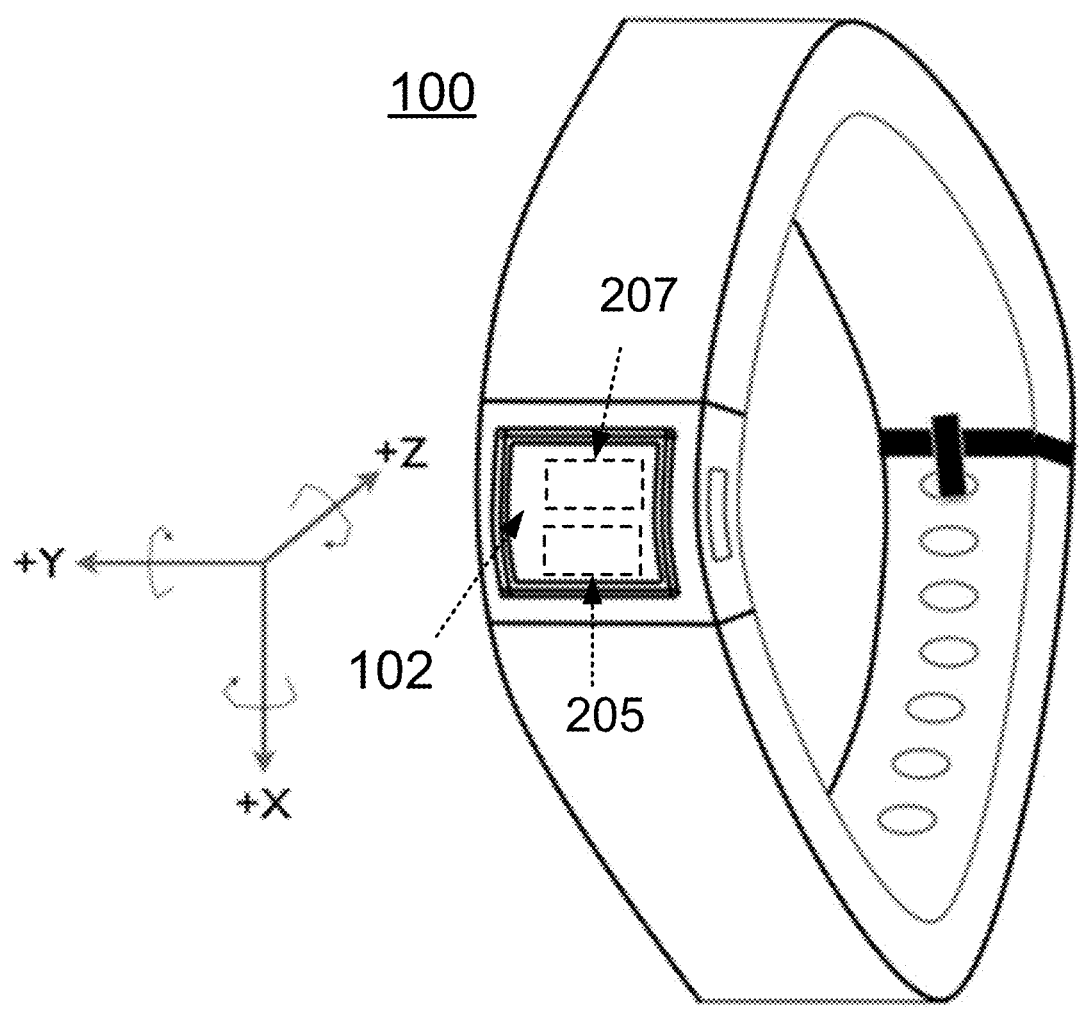
FIG. 3 illustrates a wearable device and axes around which motion is determined according to one embodiment.

FIGS. 2 and 3 illustrate other views of an embodiment of the wearable device 100. The illustrated views include the fastening system 101 and the display 102. As shown in FIGS. 2 and 3, the wearable device 100 also includes a motion system 207, one or more heart rate sensors (generally a heart rate sensor) 209, and one or more processors (generally a processor) 205. The motion system 207 includes one or more motion sensors, which includes, for example, an accelerometer, a gyroscope, or a magnetometer. The motion system 207 detects motion of the device 100 by measuring rotational acceleration, motion, position, and/or changes in rectilinear or rotational speed of the device 100. In one embodiment, the motion system 207 detects motion of the device 100 in three axes. FIG. 3 illustrates example axes X, Y, and Z relative to which the motion data is determined by the motion system 207. As shown in FIG. 3, one embodiment of the motion system 207 measures linear motion along the X, Y, and Z axes, as well as rotation around each of the axes.

The heart rate sensor 209 measures heart rate of the user of the device 100. In one embodiment, the heart rate sensor 209 includes an optical sensing system, which comprises one or more optical emitters and one or more optical sensors. The optical sensing system identifies features of blood flow of the user, enabling the detection of heart beats and thus heart rate. In one embodiment, the optical sensing system comprises one optical emitter and two optical sensors. Example optical emitters include light emitting diodes (LEDs) and lasers. Optical emitters emit light in the yellow-green portion of the spectrum (500-600 nanometers (nm)). In other embodiments light in the visible spectrum, such as blue and red, or the infrared spectrum may be used instead of or in addition to green light. The optical sensor(s) detects light in the wavelengths of light emitted by the optical emitter(s). An example optical sensor is a light-to-voltage (LTV) sensor such as a Taos TSL13T or similar.

The heart rate sensor 209 may measure the user's heart rate using techniques other than optical sensing. For example, other embodiments of the heart rate sensor 209 include an electrocardiogram (ECG) sensor or a pulse pressure sensor.

The processor 205 receives data from the motion system 207 and identifies activities of the user wearing the device 100. Example processors 205 include the TIMSP430 from TEXAS INSTRUMENTS and ARM Cortex-M class microcontrollers. Although a single processor 205 is shown in FIG. 2, the operations of the processor 205 can be performed by multiple processors 205. In general, the processor 205 uses motion data received from the motion system 207 to automatically determine an activity in which the user is engaged, without requiring explicit input from the user. As described herein, the processor 205 in some embodiments determines the activity in which a user is engaged using only the data generated by the motion system 207. Depending on the type of activity being detected, the processor 205 uses one or more of the magnitude of the motion of the device 100, the orientation of the device 100, and the frequency content of the motion to determine the user's activity.

In one embodiment, the processor 205 determines whether a user is walking or running based on the magnitude of the motion of the device 100 and frequency content of the motion. The processor 205 uses the magnitude and frequency to classify the user's activity as running or walking. For example, if the magnitude of motion and frequency of the user's steps both exceed a corresponding threshold, the user is determined to be running. If one or both of the magnitude and frequency are below the corresponding threshold, the user is determined to be walking.

The processor 205 also determines when a user is bicycling using the magnitude and frequency content of the motion data received from the motion system 207. The orientation of the device 100 may also be used to determine bicycling. In one embodiment, the processor 205 inputs the magnitude, frequency content, and device orientation into a bicycling identification algorithm, which generates a score indicative of a likelihood the user is bicycling. When the score exceeds a threshold, the user is determined to be bicycling. The bicycling identification algorithm is, for example, a model trained to classify motion data as bicycling or not bicycling based on the magnitude of the motion data, the frequency content, and the device orientation.

The various components of the device 100 illustrated in FIGS. 1 through 3 may alternatively be components of two or more devices communicatively coupled by wired or wireless communication, rather than enclosed within a single device. Furthermore, the wearable device 100 may include additional components not shown in FIGS. 1 through 3. For example, one embodiment of the wearable device 100 includes a temperature sensor and a skin conductance sensor measuring sweating of the user. The device 100 may also include a global positioning system (GPS) sensor to determine the location of the user. Other embodiments of the device 100 may include fewer, additional, or different components.

Example Processing Configuration—Running Vs. Walking

Figure 4:
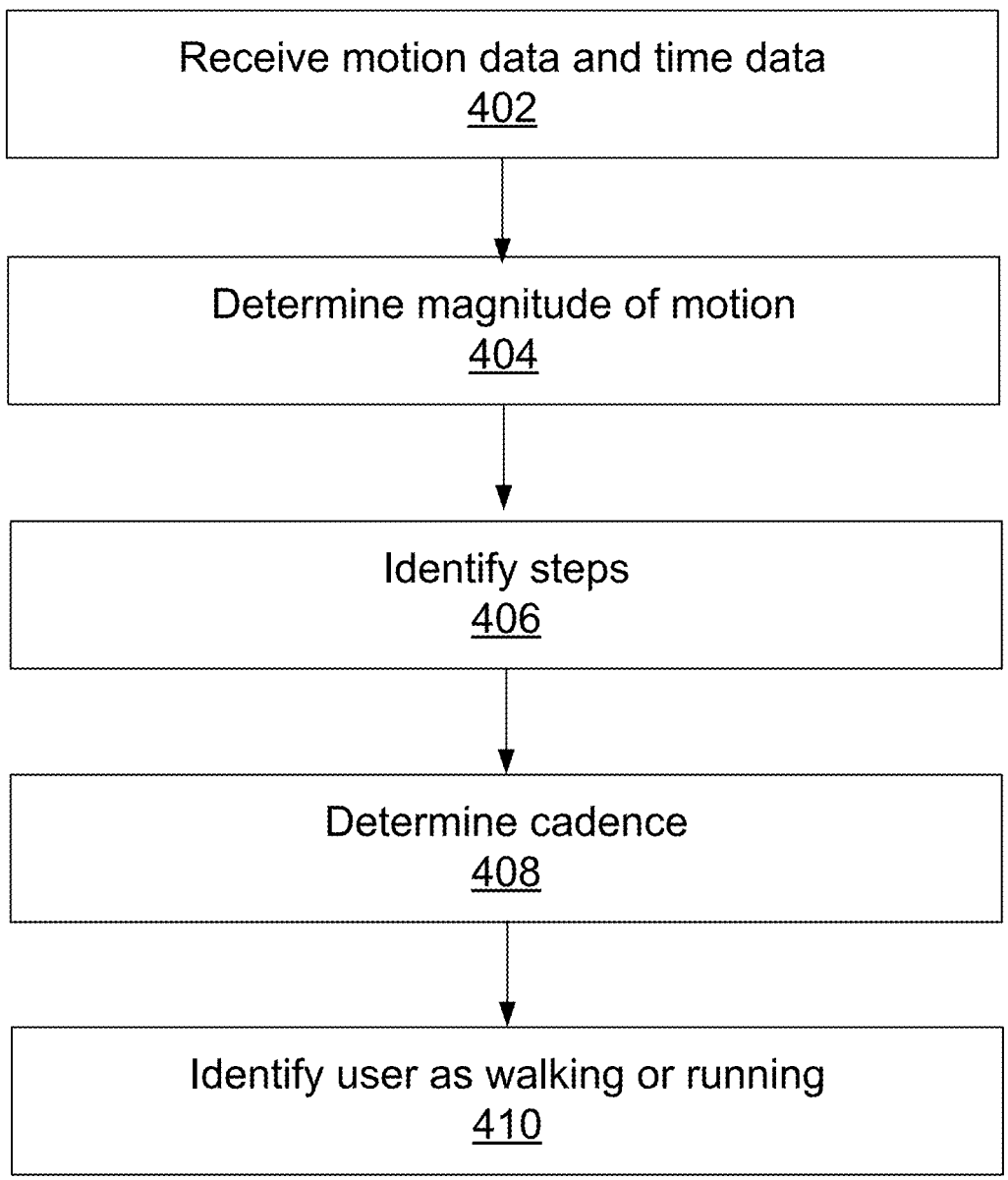
FIG. 4 is a flowchart illustrating a process for differentiating walking from running according to one embodiment.
Figure 5:
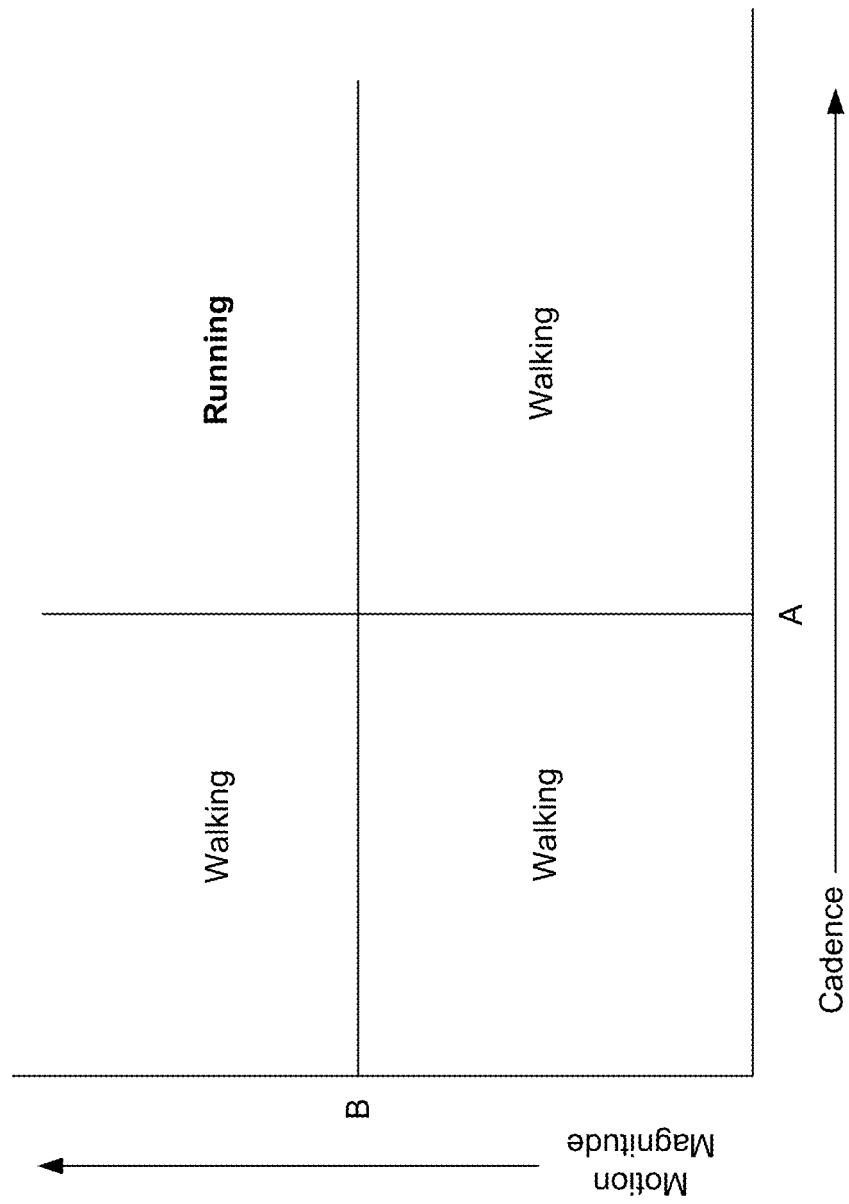
FIG. 5 illustrates a graph for analyzing motion data to identify running according to one embodiment.
Figure 6:
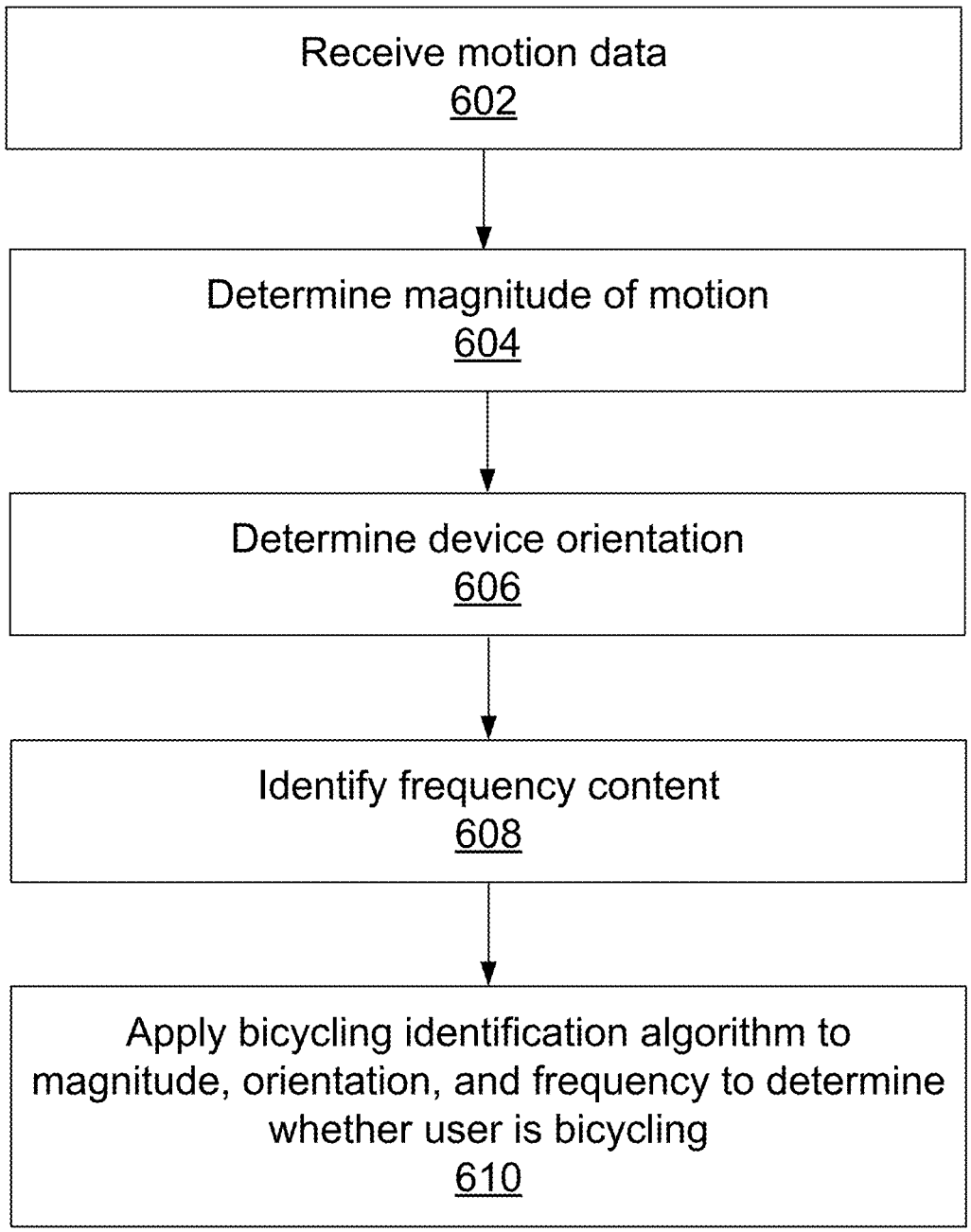
FIG. 6 illustrates a flow chart for identifying when a user is bicycling according to one embodiment.

Referring now to FIGS. 4 and 5, illustrated is a method performed by the processor 205 for identifying when a user is engaged in one type of activity as opposed to another type of activity, e.g., running as opposed to walking. For the purpose of the disclosed method, running is bipedal motion during which there are periods of time when both of the user's feet are out of contact with the ground at the same time. Walking is bipedal motion during which at least one foot is in contact with the ground at all times. Other embodiments of the method may include fewer, additional, or different steps than shown in FIG. 4, and the steps may be performed in different orders.

The processor 205 receives 402 motion data from the motion system 207. The motion data is, for example, measured by an accelerometer, and includes data in three axes. The processor 205 analyzes the received motion data to determine 404 magnitude of the motion of the device 100. In one embodiment, the processor 205 determines 404 the magnitude of the motion by taking the magnitude of an acceleration signal, applying a high-pass filter to the acceleration signal, and integrating the magnitude of the high-passed signal over a window. In another embodiment, the processor 205 determines 404 the magnitude by integrating the standard deviation of the high-passed acceleration signal over a window.

Using the received motion data, the processor 205 identifies 406 steps. Generally, steps taken by the user of the device 100 result in a periodic signal in the magnitude of the acceleration data, with each period corresponding to a step. When the magnitude change exceeds a threshold and the periods are sufficiently regular, stepping is identified. In one embodiment, the processor 205 measures a period as a time between peaks of the magnitude and identifies stepping if the variation in the periods is less than a threshold. In another embodiment, the processor 205 determines frequency content of the motion signal and identifies steps if a frequency or band of frequencies carries a threshold amount of energy. Based on the period of the identified stepping, the processor 205 determines 408 a cadence of the user's steps (that is, a number of steps taken per unit time). The cadence can be measured using any unit of time such as seconds, minutes, or hours. In some embodiments, a user's cadence is further determined using data from a gyroscope in addition to accelerometer data. Data from a magnetometer may additionally or alternatively be used to determine the cadence. In one embodiment, the processor 205 periodically determines 408 the user's cadence by segmenting the received motion data into finite windows. For example, the processor 205 determines the user's cadence on a minute-by-minute basis, calculating the number of steps taken during each minute of measurement.

The processor 205 uses the magnitude of the motion of the device 100 and the cadence of the user's steps to identify 410 a walking or running activity. Running is differentiated from walking based on the magnitude of the motion data and the determined cadence of steps. In particular, when a user is running, the magnitude of the motion data and the cadence are typically higher than those of a user walking. FIG. 5 is a schematic illustrating magnitudes and cadence used to distinguish between walking and running. As illustrated in FIG. 5, when a user's cadence exceeds a threshold A and the magnitude of the motion data exceeds a threshold B, the user is running. If only one of the cadence and the magnitude of motion data exceed their respective thresholds, the user is identified as walking. The regions of running and walking shown in FIG. 5 can be set using functions of the input variables, instead of thresholds on both variables.

The processor 205 monitors the motion system 207 data and updates the user's status from running to walking or vice versa as needed. In some embodiments, the user's status is updated from running to not running in response to the data falling into a "walking" quadrant in FIG. 5. In other embodiments, the user's status is only set to not running when both the cadence and the magnitude of the motion data are low. In other embodiments, the processor 205 identifies the user's status on a periodic basis using a hysteresis model. For example, if a threshold number of determinations immediately previous to the current determination indicated the user was running, then both cadence and magnitude of the motion data need to be low to change the user's status to not running. However, if the user's status is running but the immediately previous determination(s) include data where the user's data indicated walking with high cadence or walking with high motion magnitude, then an additional determination of walking with high cadence or walking with high motion magnitude are sufficient to change the user's status to not running Example Processing Configuration—Bicycling Referring now to FIGS. 6 through 14, illustrated is a method performed by the processor 205 for identifying when a user is bicycling. In general, the method for identifying bicycling includes an analysis of data collected over one or more windows of time, also referred to as epochs. Windows of time can be from 15 to 120 seconds, or an amount of time in between (e.g., 30, 45, 60, 75, 90, or 105 seconds). Each window of time can be separated from another window of time by some amount of time, adjacent to the next window of time, or overlapping another window of time. When using overlapping windows, the amount of time of overlap between windows can vary. In some embodiments, a new window starts every 15, 30, 45, 60, 90, or 105 seconds. For example, if windows are 60 seconds, a new window could start after 15, 30, or 45 seconds, resulting in 45 seconds, 30 seconds, or 15 seconds of overlap, respectively. Similarly, for a 90 second window, a new window could start after 15, 30, 45, 60, or 75 seconds. In some embodiments, multiple windows of data may be analyzed to improve the accuracy of detecting bicycling. For example, if a user frequently stops moving (e.g., while bicycling in a city and stopping frequently for traffic lights), analysis of one window of data may not be sufficient to accurately identify that a user is bicycling. Other embodiments of the method may include fewer, additional, or different steps than shown in FIG. 6, and the steps may be performed in different orders.

Figure 7:
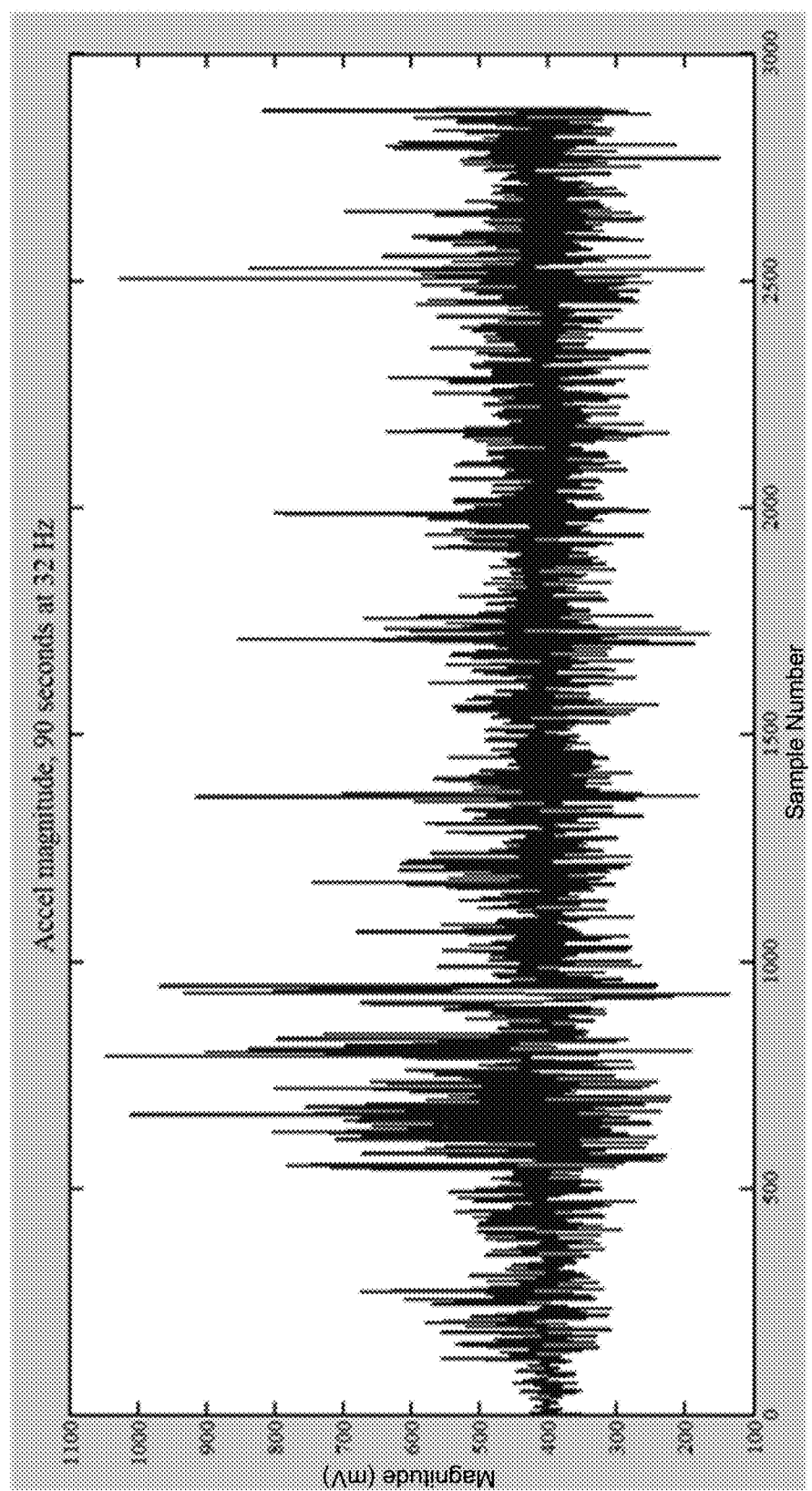
FIG. 7 illustrates an exemplary accelerometer magnitude signal measured over a 90 second window.
Figure 8:
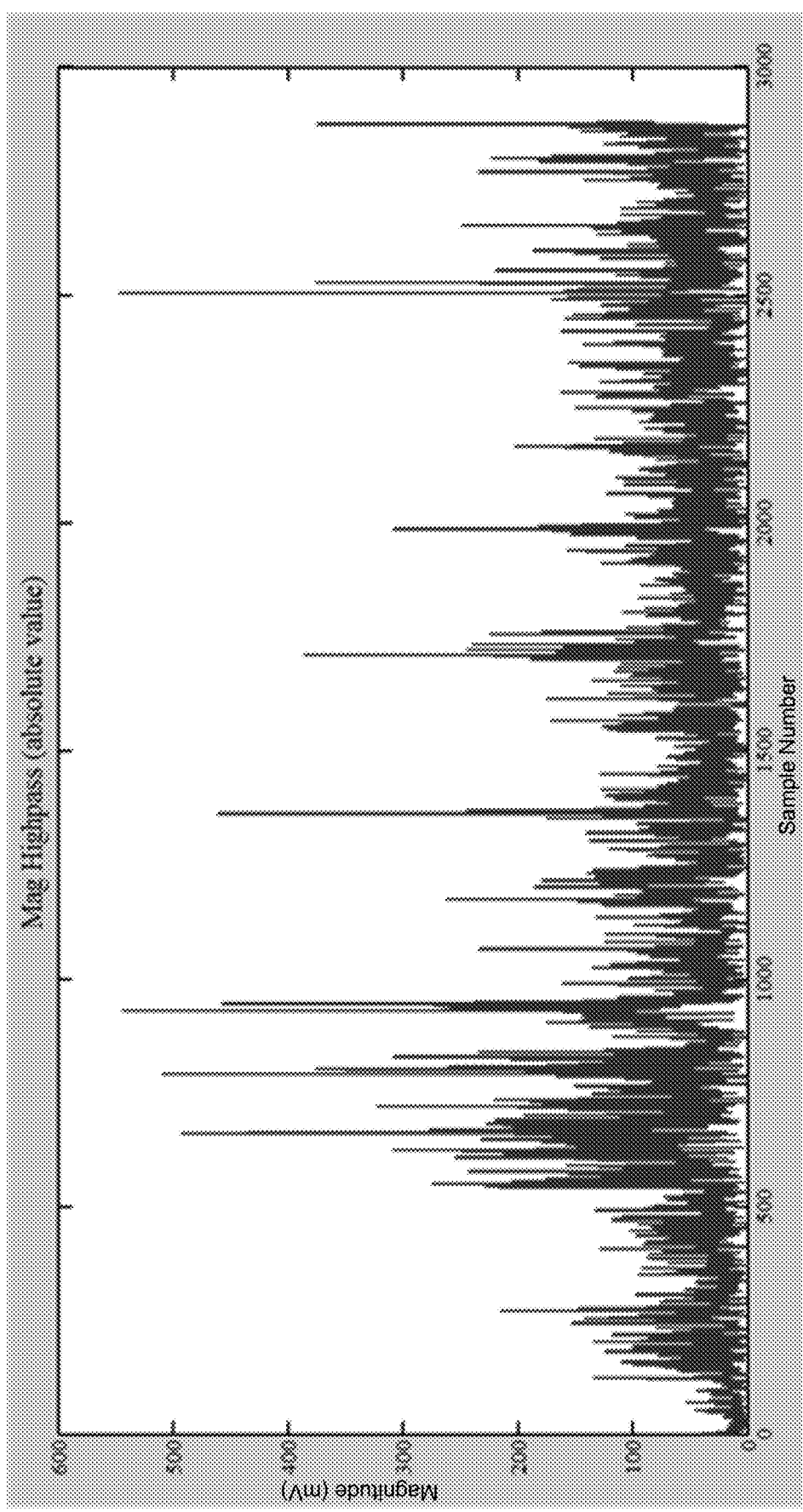
FIG. 8 illustrates the signal from FIG. 7 after high-pass filtering and determination of the absolute value.
Figure 9:
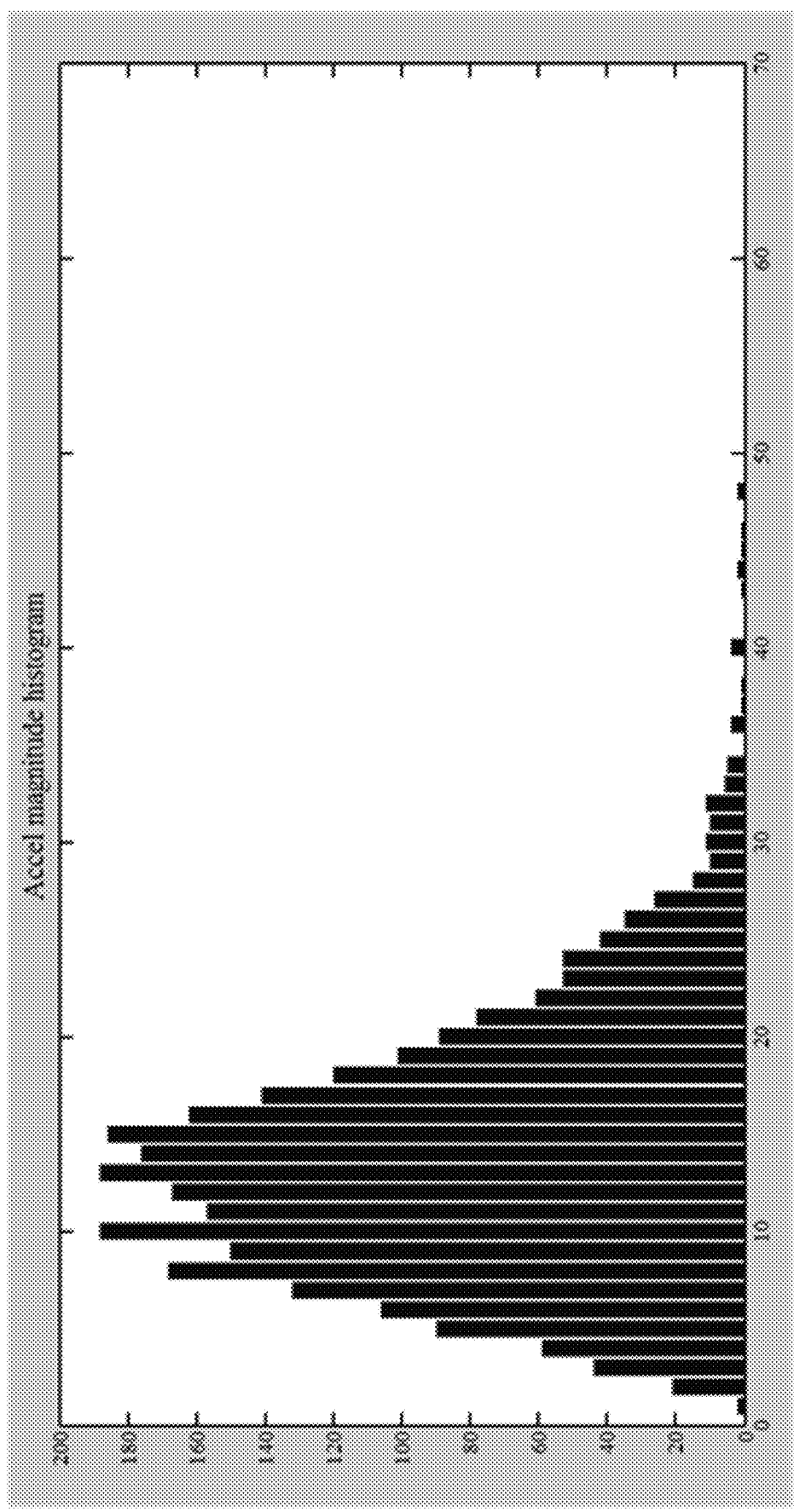
FIG. 9 illustrates a histogram of the signal in FIG. 8 divided into 64 bins.
Figure 10:
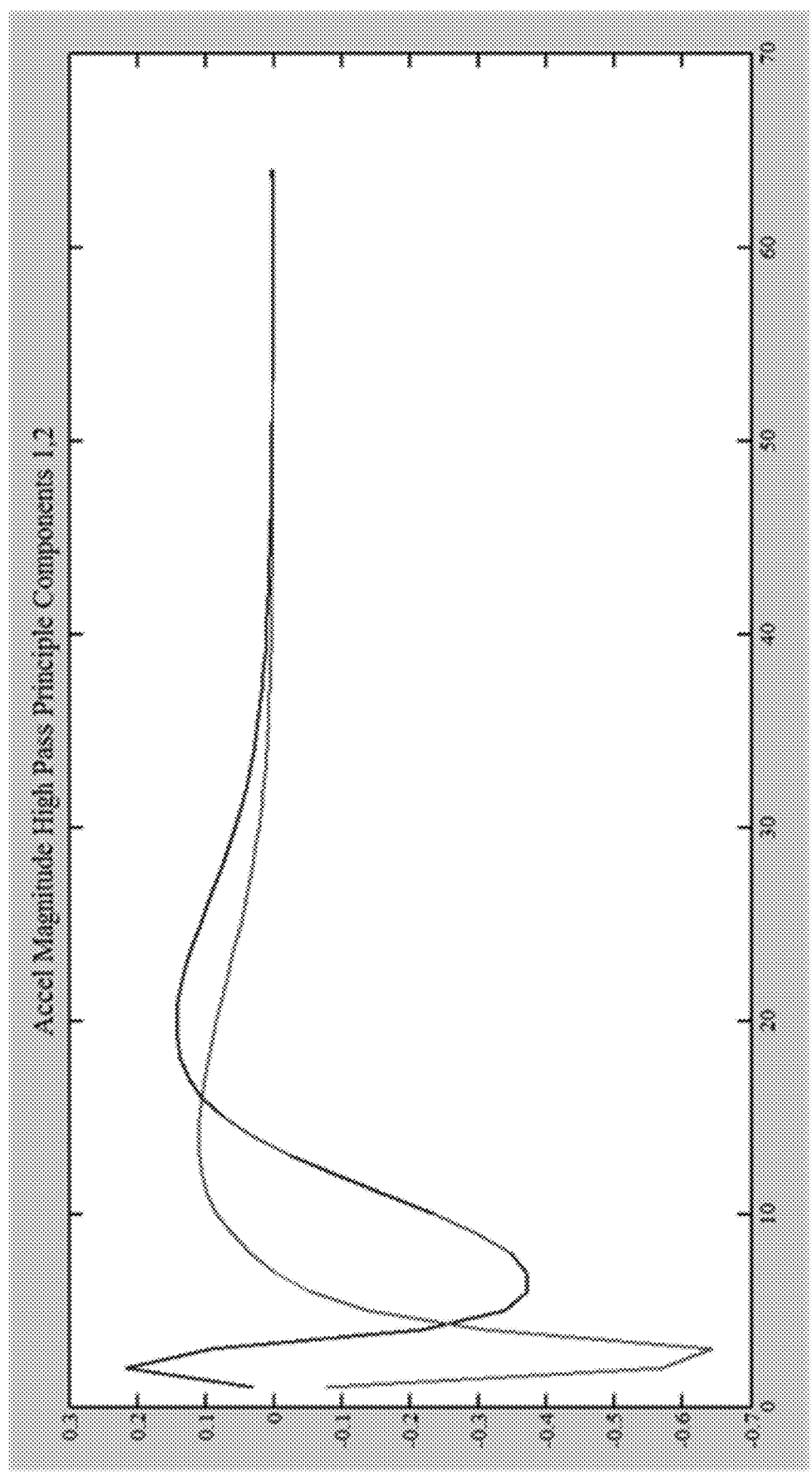
FIG. 10 illustrates the principal components 1 and 2 in the signal of FIG. 8.

The processor 205 receives 602 motion data from the motion system 207 collected during one or more windows of time, and determines 604 the magnitude of the motion. The magnitude of the motion of the device 100 is useful for identify the user of the device 100 is bicycling, as the magnitude represents both a motion traversing a distance as well as vibrations the user undergoes while bicycling. Vibrations that are typical for a user bicycling may not be present for a user walking or running, and therefore may be used by the processor 205 to help determine the user is bicycling. To determine 604 the magnitude of the motion of the device 100, one embodiment of the processor 205 generates a histogram of the device motion and reduces the dimension of the histogram. FIG. 7 illustrates an exemplary accelerometer magnitude signal measured over a 90 second window. In some embodiments, the signal is high-pass filtered. FIG. 8 illustrates the absolute value of the signal from FIG. 7 after high-pass filtering. When the magnitude is analyzed over time, the processor 205 generates a histogram of the signal from the motion system 207 during the specified period of time. The histogram's dimensions are reduced while preserving the information relevant to the analysis of whether a person is riding a bicycle. The dimensions can be reduced by projecting the results of the histogram vector onto a different vector. This vector can be determined using principal component analysis (PCA) and a dataset of histograms. Other techniques for reducing dimensions can alternatively be used, such as independent component analysis (ICA). FIG. 9 illustrates a histogram of the signal in FIG. 8 divided into 64 bins. Either the one-time magnitude or the top principal components identified by the PCA are used in the bicycling identification algorithm. In some embodiments, 1, 2, 3 or 4 principal components are used, corresponding to reducing the dimensions of the histogram to 1, 2, 3 or 4 variables. FIG. 10 illustrates the principal component vectors 1 and 2.

The processor 205 also analyzes the motion data received from the motion system 207 to determine 606 the orientation of the wearable device 100. In one embodiment, identification of a user bicycling assumes that the user is wearing the device 100 on a wrist, although similar analyses may be carried out for devices configured to be worn or carried at locations other than the wrist. The positions of the wrist when a person is riding a bicycle are different from the position of the wrist during other activities in which a person may be engaged. Furthermore, depending on the type of handlebars on the bicycle and the manner in which the user grips the handlebars, there are different positions for the wrist in space. Thus, the wrist position is useful in the bicycling identification algorithm and the processor 205 determines the orientation of the device 100 to determine the wrist position.

To determine 606 the device orientation, the processor 205 extracts one measurement from each of the accelerometer channels (e.g., an x-orientation, a y-orientation, and a z-orientation). In one embodiment, the processor 205 extracts one sample within in a window from each accelerometer channel, and uses each sample as the measurement of the orientation. In another embodiment, the processor 205 computes an average value of the signal received from each accelerometer channel during a window of time, and uses the average value as the measurement of orientation.

Figure 11:
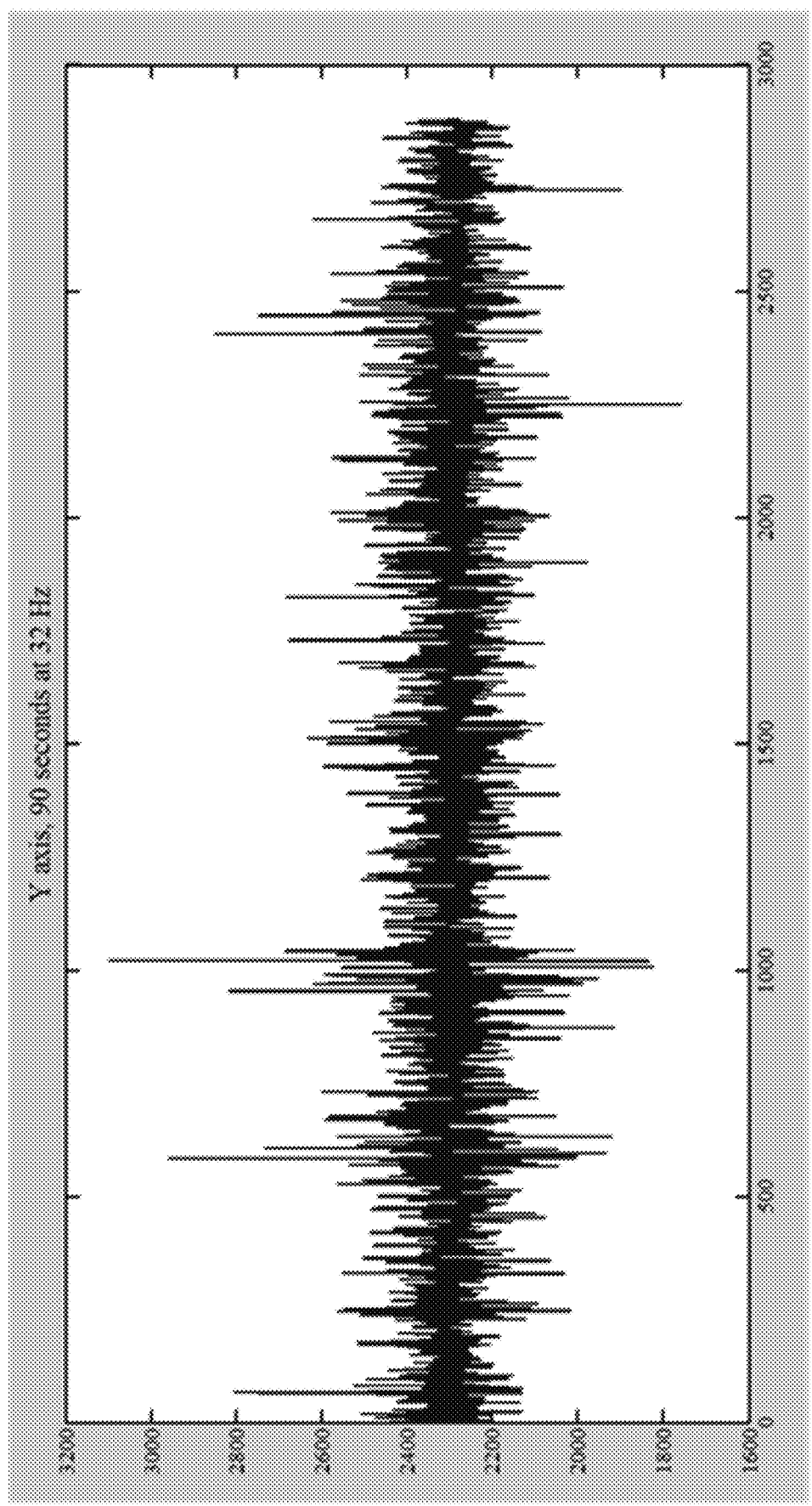
FIG. 11 illustrates the signal from the motion system 207 along the y-axis for a 90-second period.
Figure 12:
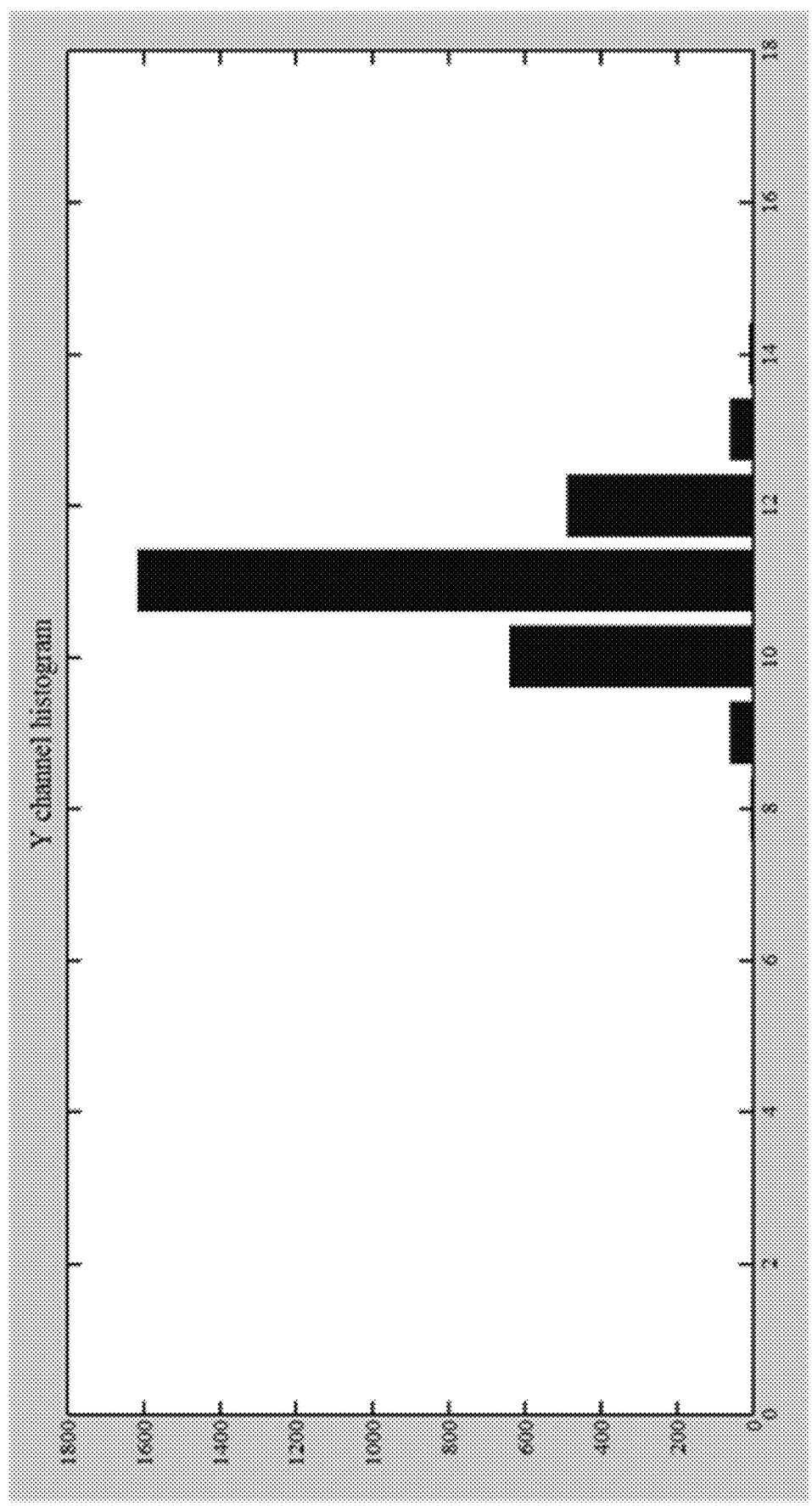
FIG. 12 illustrates a histogram of the signal in FIG. 11.
Figure 13:
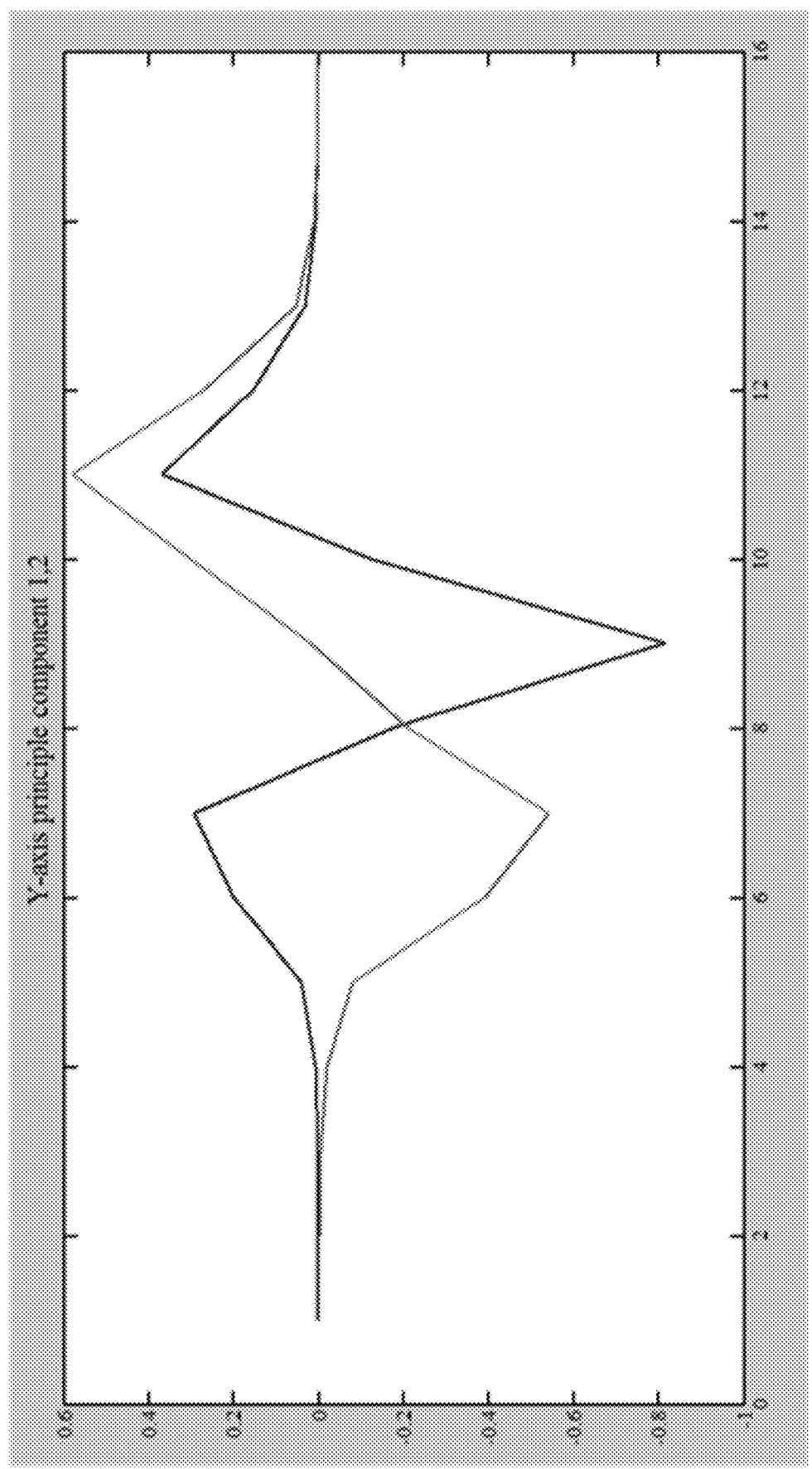
FIG. 13 illustrates principal components 1 and 2 in the signal of FIG. 11.

In yet another embodiment, the processor 205 generates a histogram of the data received from each accelerometer channel for a window of time, calculates the mean of the histogram, and uses the determined mean as the measurement of the orientation. The processor 205 may reduce the dimensions of the histogram (e.g., using PCA) prior to calculating the mean. As an example, FIG. 11 illustrates the signal from the motion system 207 along the y-axis for a 90-second period. FIG. 12 illustrates a histogram of the signal in FIG. 11, and FIG. 13 illustrates principal component vectors 1 and 2. As in the analysis of the magnitude of motion, other techniques for reducing the dimensions of the histogram can be used. The data from the motion system 207 along the x and z axes are processed in a similar fashion. The determined principal components are entered into the bicycling identification algorithm.

The processor 205 also analyzes the received motion data to identify 608 frequency content of the motion signal. In analyzing the signal, the processor 205 identifies various dominant frequencies in the signal as well as the power of the signal. In some embodiments, a signal from each channel of the accelerometer (corresponding to the X, Y, and Z axes) as well as the overall magnitude of the motion signal is analyzed. Dominant frequencies are identified from multiple frequency zones of the signal. In some embodiments, the data is divided into low and high frequency portions and a dominant signal is identified for each. In other embodiments, the data is divided into additional frequency windows and a dominant frequency identified for each.

Figure 14:
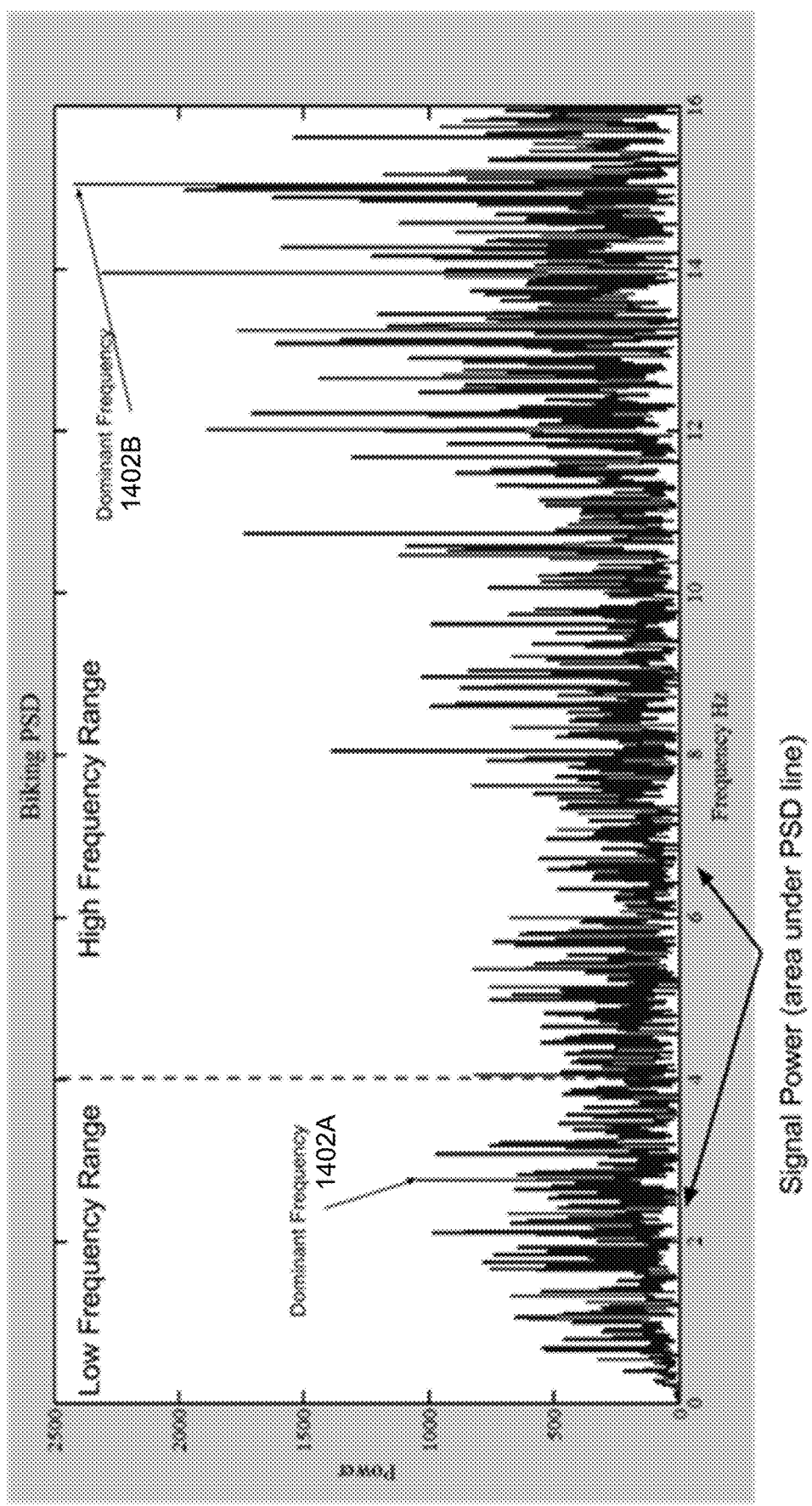
FIG. 14 illustrates a plot of power spectral density (PSD) determined from a Fourier transform of the data from a window.

FIG. 14 illustrates a plot of power spectral density (PSD) determined from a Fourier transform of the data from a window. The data illustrated in FIG. 14 has been high-passed. The spectrum is divided into a high frequency portion and a low frequency portion as indicated by the dotted line in FIG. 14, and a dominant frequency is identified for each portion. The dominant frequency is the frequency with the highest power. For example, FIG. 14 illustrates a dominant frequency 1402A from the low frequency range and a dominant frequency 1402B from the high frequency range. In one embodiment, the processor 205 determines the power of the signal by measuring the area under the PSD line. In another embodiment, the processor 205 band-passes the signal for each frequency window of interest and uses time domain techniques to obtain signal power and dominant frequency. For example, signal power can be determined by taking the standard deviation of a signal, or, if the signal is high passed, summing the area under the absolute value of the signal. The dominant frequency can be estimated by counting the number of zero crossings of a high passed signal. An alternative to frequency domain processing is to band-pass the signal to a frequency range [f1, f2] (where the range [f1, f2] defines a region of interest F) and computing the power of the resulting signal to determine strength in the specified frequency band.

The processor 205 applies 610 a bicycling identification algorithm to the determined magnitude of motion, orientation of the device 100, and frequency content to determine if the user of the device 100 is bicycling. In one embodiment, the bicycling identification algorithm is a support vector machine. In an example, bicycling is determined by entering the following inputs: dimension reduced histogram results using principal components 1 (A) and 2 (B) of the motion magnitude determined as described in relation to FIGS. 7-10; reduced dimension histogram results using principal components 1 (C) and 2 (D) of the Y-axis motion signal determined as described in relation to FIGS. 11-13; the dominant frequencies for the motion signal for both high (E) and low (F) frequencies; the dominant frequency of the low frequency signal for X, Y and Z axes (G); the dominant frequency of the high frequency signal for the Z axis (H); and the signal power for the low frequency signals for the X, Y and Z axes (I). These are combined into a feature vector as follows:

[A,
B,
C,
D,
E,
H,
F,
G,
I]

Similar feature vectors are extracted from a training set of windows (that is, windows of motion data each labeled as biking or not biking) and used to determine a classification vector defining a decision boundary for a support vector machine. The feature vector for an unclassified window of motion data is projected onto the classification vector. For example, a dot product is taken between the feature vector and the following example classification vector:

[5.77,
8.19,
−4.98,
−0.25,
−11.62,
−4.11,
−6.69,
7.59,
−6.11]

If the result of the dot product is greater than a threshold, the window is classified as a window of bicycling data. In contrast, if the result of the dot product is less than the threshold, the window is classified as not being a window of bicycling data.

In some embodiments, the processor 205 identifies the user as bicycling during a window classified as bicycling data. In other embodiments, the processor 205 analyzes multiple windows of data with the bicycling identification algorithm in order to identify a user as bicycling. In such an embodiment, the processor 205 identifies a user as bicycling when a number of consecutive windows of motion data are classified as bicycling data. For example, the processor 205 determines the user of the device 100 is bicycling if 3, 4 or 5 consecutive windows of motion data are classified as bicycling data. In other embodiments, the processor 205 identifies a user as bicycling when a majority of a group of consecutive windows of motion data are classified as bicycling data. Examples include 2/3, 3/4, 3/5, 4/5, 4/6 windows classified as bicycling data.

The processor 205 may also use the same analysis as described above and monitors when the score from the bicycling identification algorithm is below the threshold for identifying a user as bicycling. In one embodiment, the processor 205 identifies a user as no longer bicycling when a number of consecutive windows of motion data are classified as not bicycling. Alternatively, the processor 205 identifies a user as not bicycling when a majority of a group of consecutive windows of motion data are classified as not bicycling. Examples include 2/3, 3/4, 3/5, 4/5, 4/6 scores as negative for bicycling. In some embodiments, the threshold for the bicycling identification algorithm scores to identify a user as still bicycling is lower than the threshold for identifying a user as bicycling when the user is not currently identified as bicycling. Additionally or alternatively, when the processor 205 uses a plurality of determinations to identify a user as bicycling, more consecutive scores (or a larger portion of scores) identifying the user as not bicycling are required to change the user from bicycling to not bicycling as opposed to those required to identify a user as bicycling when they were not previously identified as bicycling. In this case, the processor 205 detects fewer false bicycling negatives.

In some embodiments, the device 100 identifies whether a user is seated on the bicycle saddle, or seat, or whether the user is pedaling in a standing position. This is determined from the position of the wrist, as well as the dominant frequencies in the acceleration magnitude signal. This is the result of the device 100 having a different position because of a higher body position of the user relative to the bike, and larger frequency contribution from the user pedaling from a standing position. In some embodiments the user's position as standing or sitting is stored for later retrieval by the user to analyze the user's performance on a bicycle ride.

In some embodiments, the determination of bicycling further includes data from a gyroscope. This provides for additional data to assess the position of the user's wrist and whether a user is standing or sitting on the bicycle.

Example Processing Configuration—Use Cases

In response to a determination that a user is walking, running, or bicycling the processor 205 can automatically initiate various processes. For example, the processor 205 can start a timer to time the identified activity so that the user does not have to manually start a timer. The processor 205 can also initiate analysis that is specific to an activity. Optionally, the processor 205 displays the results of the activity-specific analysis on the display 102.

In some embodiments, the data collected by wearable device 100 is further used to determine an amount of calories expended by the user wearing the device. Different activities burn different amounts of calories per unit time and thus in some embodiments, the identified activity, such as running, walking, or bicycling, is used in the determination of calories expended by the user. In some embodiments, the processor 205 determines the calories expended and in other embodiments, a remote processor determines the calories expended after receiving data collected by the device 100. In some embodiments, the amount of calories expended is determined by accessing a table of caloric expenditure data specific to the determined activity. Alternatively, the processor 205 or remote processor selects a function to determine caloric expenditure based on the determined activity.

The motion data used for determining caloric expenditure can be based on multiple sensors or motion including an accelerometer, a gyroscope, and/or a magnetometer. In some embodiments, the determination of caloric expenditure is further based on other parameters of the user, such as heart rate, temperature, and sweating. In some embodiments, the determination of caloric expenditure is a function of both the activity in which a user is engaged and a general level of exertion. As is known in the art, caloric expenditure varies within a single activity, such as bicycling, depending on the user's level of exertion.

The processor 205 may use any of a variety of sensors of the wearable device 100 to determine an exertion level of the user. In one embodiment, the processor 205 uses a heart rate of the user (e.g., as measured by the heart rate sensor 209) to determine a level of exertion of the user. In another embodiment, the processor 205 uses the user's location (e.g., as indicated by a global positioning sensor of the device 100) to determine a level of exertion of the user. For example, the user's location indicates a grade of the route the user is on. If the user is bicycling or running uphill, the processor 205 determines the user to be at a higher exertion level than when the user is bicycling or running downhill or on flat land.

In yet another embodiment, exertion is analyzed by assessing the amount of sweat the user is generating. For example, a user generating a greater amount of sweat is determined to be exercising at a higher exertion level than when the user generates less sweat. The user's skin temperature may additionally or alternatively be used to determine exertion. For example, a higher exertion level corresponds to a higher skin temperature and larger difference between the user's skin temperature and the ambient temperature. Furthermore, data from a magnetometer can also be used to determine a level of exertion. For example, a magnetometer can identify wind effects and identify the absolute incline of the user's path, both of which are relevant to determining exertion of a user walking, running, or bicycling.

Additional Configuration Considerations

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for identification of activities in which a user is engaged through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method comprising:
    receiving motion data collected by a motion sensor worn by a user during an activity;
    determining a magnitude of the motion data by taking the magnitude of an acceleration signal, applying a high-pass filter to the acceleration signal, and integrating the standard deviation of the high-passed acceleration signal over a period of time;
    determining a frequency of the motion data; and
    identifying the activity based on the magnitude and the frequency of the motion data.

2. The method of claim 1 further comprising:
    determining the frequency of the motion data by determining a cadence of steps taken by the user;
    responsive to the cadence exceeding a cadence threshold and the magnitude of the motion data exceeding a magnitude threshold, identifying the activity as running; and
    responsive to at least one of the cadence and magnitude being less than a corresponding threshold, identifying the activity as walking.

3. The method of claim 2 further comprising:
    after identifying the activity as running, detecting at least one of the cadence falling below the cadence threshold and the magnitude of the motion data falling below the magnitude threshold; and
    responsive to the detection, identifying the activity as walking.

4. The method of claim 2, wherein the cadence is determined using a period of the magnitude of the motion data.

5. The method of claim 1 further comprising:
    determining an orientation of the wearable device; and
    identifying the activity as bicycling based on the magnitude and the frequency of the motion data and the orientation of the wearable device.

6. The method of claim 5 further comprising:
    determining a dominant frequency of a first frequency range of the motion data and a dominant frequency of a second frequency range of the motion data.

7. The method of claim 6 further comprising:
    applying a trained classifier to the magnitude of the motion data, the orientation of the wearable device, the dominant frequency of the first frequency range, and the dominant frequency of the second frequency range, the classifier generating a score indicating a likelihood that the user is bicycling; and
    responsive to the score exceeding a threshold, identifying the activity as bicycling.

8. The method of claim 1 further comprising:
    automatically starting a timer to time the activity responsive to identifying the activity.

9. The method of claim 1 further comprising:
    determining a caloric expenditure of the user during the activity based at least in part on the identified activity.

10. A computer program product comprising a tangible non-transitory computer readable storage medium containing computer program instructions for identifying an activity in which a user is engaged, the computer program instructions executable by a processor to:
    receive motion data of the user collected by a wearable device worn by the user during the activity;
    determine a magnitude of the motion data by taking the magnitude of an acceleration signal, applying a high-pass filter to the acceleration signal, and integrating the standard deviation of the high-passed acceleration signal over a period of time;
    determine a frequency of the motion data; and
    identify the activity based on the magnitude and the frequency of the motion data.

11. The computer program product of claim 10, wherein the computer program instructions executable by the processor to determine the frequency of the motion data comprise computer program instructions executable by the processor to determine a cadence of steps taken by the user, and wherein the computer program instructions executable by the processor to identify the activity comprise instructions executable by the processor to:
    responsive to the cadence exceeding a cadence threshold and the magnitude of the motion data exceeding a magnitude threshold, identify the activity as running; and
    responsive to at least one of the cadence and magnitude being less than a corresponding threshold, identify the activity as walking;
    after identifying the activity as running, detect at least one of the cadence falling below the cadence threshold and the magnitude of the motion data falling below the magnitude threshold; and
    responsive to the detection, identify the activity as walking.

12. The computer program product of claim 10, wherein the computer program instructions executable by the processor to identify the activity comprise computer program instructions executable by the processor to:
    determine an orientation of the wearable device; and
    identify the activity as bicycling based on the magnitude and the frequency of the motion data and the orientation of the wearable device.

13. The computer program product of claim 12, wherein the computer program instructions executable by the processor to determine the frequency of the motion data comprise computer program instructions executable by the processor to:
  determine a dominant frequency of a first frequency range of the motion data and a dominant frequency of a second frequency range of the motion data.

14. The computer program product of claim 13, wherein the computer program instructions executable by the processor to identify the activity as bicycling comprise computer program instructions executable by the processor to:
  apply a trained classifier to the magnitude of the motion data, the orientation of the wearable device, the dominant frequency of the first frequency range, and the dominant frequency of the second frequency range, the classifier generating a score indicating a likelihood that the user is bicycling; and
  responsive to the score exceeding a threshold, identify the activity as bicycling.

* * * * *